(12) United States Patent
Oost et al.

(10) Patent No.: US 6,329,554 B1
(45) Date of Patent: Dec. 11, 2001

(54) CONTINUOUS PREPARATION OF UNSATURATED KETONES

(75) Inventors: Carsten Oost, Bad Dürkheim; Manfred Stroezel, Ilvesheim; Heinz Etzrodt, Neustadt; Dietmar Weller, Ludwigshafen; Bernhard Bockstiegel, Römerberg; Klaus Reimer, Mutterstadt; Gerd Kaibel, Lampertheim; Hagen Jaedicke, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/391,619

(22) Filed: Sep. 7, 1999

(30) Foreign Application Priority Data

Sep. 7, 1998 (DE) .............................. 198 40 747

(51) Int. Cl.[7] .................................................. C07C 45/00
(52) U.S. Cl. .................. 568/406; 568/383; 568/388; 568/391
(58) Field of Search .................................... 568/391, 346, 568/398, 356, 383, 388, 406

(56) References Cited

U.S. PATENT DOCUMENTS 4,310,705 * 1/1982 Nissen et al. .................... 568/391
6,051,741 * 4/2000 Etzrodt et al. ................... 568/406

* cited by examiner

Primary Examiner—Sreeni Padmanabhan
(74) Attorney, Agent, or Firm—Oblon, Spivak, McClelland, Maier & Neustadt, P.C.

(57) ABSTRACT

Process for the continuous preparation of unsaturated ketones of the formula I

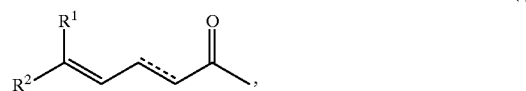

(I)

where the dashed line can be an additional C—C bond, $R^1$ is an alkyl, and $R^2$ is an aliphatic hydrocarbon having from 1 to 37 carbons, a cycloalkyl or a cycloalkylalkyl, by reacting an unsaturated alcohol of the formula II

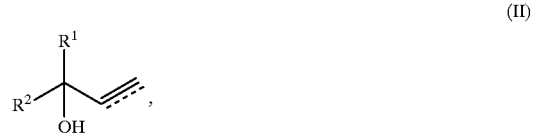

(II)

with an alkyl acetoacetate of the formula III

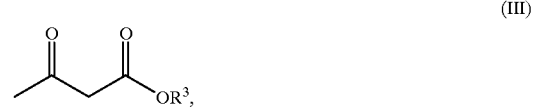

(III)

where $R^3$ is an alkyl having from 1 to 5 carbons, in the presence or organic aluminum compounds as catalyst.

13 Claims, 2 Drawing Sheets

CONTINUOUS PREPARATION OF UNSATURATED KETONES

The present invention relates to an improved process for the continuous preparation of unsaturated ketones by reacting α,β-unsaturated alcohols with alkyl acetoacetates in a Carroll reaction.

The preparation of unsaturated ketones by reacting α,β-unsaturated alcohols with alkyl acetoacetates in the presence of organic aluminum compounds with elimination of the alcohol originating from the acetoacetic ester is, disregarding the improvements according to the invention, already known in its essential features. The non-catalyzed reaction between an unsaturated alcohol and an alkyl acetoacetate was described for the first time by M. F. Carroll [J. Chem. Soc. (London) 1940, pages 704 to 706]. The field of application and mechanism of this reaction were reported one year later by the same author [J. Chem. Soc. (London) 1941, pages 507 to 511].

A process method for the preparation of 6,10,14-trimethyl-5-pentadecen-2-one by transesterification of ethyl acetoacetate with 3,7,11-trimethyl-1-dodecen-3-ol in the presence of aluminum trialkoxides is given in French Patent 1 219 166. According to this process, the reactants and the catalyst are charged together into the reaction still and the reaction is carried out batchwise with the alcohol being released separated off by distillation. In this process, the desired ketone is obtained in 77% yield in a reaction time of about 10 hours.

Both the relatively long reaction times and the inadequate yields are unsatisfactory with this process for an industrial synthesis. The inadequate yields are particularly serious in the preparation of higher ketones, i.e. when use is made of higher alcohols of the formula II, since their preparation becomes increasingly expensive with increasing chain length. If attempts are made to improve the yields by using the cheaper component, here the alkyl acetoacetate, in excess, dehydroacetic acid is readily formed as by-product, which firstly deactivates the catalyst and secondly can only be separated off again with difficulty from the desired product. In addition, the dehydroacetic acid can crystallize out and thus block the outlet lines of the towers used.

A number of other patents are known which describe differing variants of what is termed this Carroll reaction. Thus, U.S. Pat. No. 2,795,617 and DE-AS 1 053 498 and CH-PS 342947 state that "although it is generally neither necessary nor desirable, a solvent can be used to moderate the exothermic reaction course". According to these patents, the aluminum trialkoxide is added to the acetoacetate of the α,β-unsaturated alcohol and the mixture is refluxed with vigorous stirring, yields up to 80% being achieved. The corresponding acetoacetate must be prepared in a preceding step. U.S. Pat. No. 2,839,579 and DE-PS 1078112 report that the thermal rearrangement of acetoacetates can be carried out in a solvent. The corresponding acetoacetates are prepared by condensing diketenes with a corresponding unsaturated alcohol in a separate step. DE-PS 1 068 696 also states that the accompanying use of a solvent could be advantageous. In all cases, high-boiling solvents are mentioned which have boiling points far above the reaction temperature.

The yields specified in these patents are unsatisfactory for an industrial application. The accompanying use of a high-boiling solvent is not generally accompanied by significant increases in yields and therefore leads to a decrease in the space-time yields. It is considerably disadvantageous that, to prepare the acetoacetates of the α,β-unsaturated alcohol, a further process step is necessary, since further costs are associated therewith.

A process for the preparation of 2-methyl-2-hepten-6-one is described in DE-AS 2 652 863. Here, alkyl acetoacetate, 3-methyl-1-buten-3-ol (methylbutenol) and the catalyst are charged into a reaction vessel having a mounted fractionation tower and then a mixture of alkyl acetoacetate and methylbutenol is added. During the reaction, the content of alkyl acetoacetate in the reaction mixture is to be no greater than 15% by weight, in order to avoid side reactions. However, a disadvantage of this process is that simple metering of alkyl acetoacetate into excess methylbutenol is not possible, since the boiling point of methylbutenol is far below the reaction temperature. The use of a high-boiling solvent decreases the space-time yield, however. The yield of 90% is unsatisfactory.

Czech Patent 216 360 describes that the Carroll reaction is carried out in a mixture of unsaturated ketone and methyl acetoacetate or ethyl acetoacetate with addition of an amount of the unsaturated alcohol which is just sufficient for the reaction. In this case, from the reaction mixture there is distilled off the carbon dioxide and a mixture of the unreacted unsaturated alcohol and methanol or ethanol, which mixture is continuously fractionated in a coupled distillation tower. The α,β-unsaturated alcohol, whose boiling point must be below 180° C., is then recirculated to the reaction. In the case of reaction times of 8 hours, yields of approximately 80% are achieved. This procedure is, according to details in this patent, advantageous, because entrainment of the two lower-boiling components from the reaction mixture by the resultant carbon dioxide cannot be avoided. The coupling described in this patent of a distillation tower to the actual reactor system is not absolutely necessary, since entrainment of the α,β-unsaturated alcohol by carbon dioxide can be avoided by correct design of the reactor system. For example, according to the process of DE 2 928 944, it is possible to separate off only methanol and carbon dioxide and to keep the α,β-unsaturated alcohol in the reaction still. Thus, mainly, additional capital and energy costs result from the coupled distillation tower. In addition, the yields and reaction times in this process are unsatisfactory. A further disadvantage of the process is the restriction of the boiling temperature of the α,β-unsaturated alcohol to below 180° C., because most of the alcohols relevant to vitamin E synthesis boil above 200° C.

In contrast to the abovementioned patents, DE 2 928 944 describes the use of a solvent whose boiling point is between that of the acetoacetic ester used and that of the alcohol being cleaved therefrom. This solvent is termed "an intermediate boiler". Possible inert intermediate boilers mentioned are appropriately boiling alcohols, esters, ethers, halogenated hydrocarbons and aromatic hydrocarbons, but preferably aliphatic ketones having from 4 to 7 carbons. As a particularly advantageous embodiment, the use of 3-methyl-1-buten-3-ol as reactive intermediate boiler is mentioned, with its reaction with the alkyl acetoacetate to form 2-methyl-2-hepten-6-one as a further product of value occurring as an additional wanted side reaction. Advantages of the use of such an intermediate boiler mentioned are increased product yields (approximately 95% based on the alcohol and approximately 85% based on the acetoacetic ester) and shorter reaction times (approximately from 4 to 5 h) and therefore high space-time yields. For a batchwise reaction procedure, a distillation still having an attached fractionation tower is proposed as a reactor system and for a continuous reaction procedure, a heated vessel cascade is proposed.

However, the use of an intermediate boiler is accompanied not only by advantages but also by the disadvantages below. When an inert intermediate boiler is used, the reactor volume available for the starting materials decreases, i.e. the achievable space-time yield must also be decreased. The use of the reactive intermediate boiler 3-methyl-1-buten-3-ol, in contrast, leads to forced coupled production of 2-methyl-2-hepten-6-one, which can be undesirable. Furthermore, the process is limited to systems in which the α,β-unsaturated alcohol boils above the alkyl acetoacetate used. The continuous process proposed in the patent requires a reactor cascade and thus high capital costs. A further disadvantage is the relatively low yield based on the alkyl acetoacetate.

It is an object of the present invention, therefore, to carry out the reaction of α,β-unsaturated alcohols with alkyl acetoacetates to form unsaturated ketones, avoiding the disadvantages of the processes of the prior art. The novel process should therefore be able to be carried out continuously in a single reactor, in which case higher product yields based on the unsaturated alcohol, and in particular higher product yields based on the alkyl acetoacetate, should be achieved with reaction times as short as possible and without using an intermediate boiler. There should in addition be no restriction with respect to the boiling points of the reactants.

In particular, the ketones which are sought after as aroma substances and intermediates of the vitamin E precursor isophytol, such as 6,10-dimethyl-5,9-undecadien-2-one (geranylacetone), 6,10,14-trimethyl-5,9,13-pentadecatrien-2-one(farnesylacetone), 6,10-dimethyl-5-undecen-2-one (dihydrogeranylacetone), 6,10,14-trimethyl-5,10-pentadecadien-2-one (dihydrofarnesylacetone) and 2-methyl-2-hepten-6-one, should be able to be prepared continuously in a reactor with higher yields and with higher space-time yields.

We have found that these objects are achieved by a process of the type described at the outset in which the unsaturated ketones of the formula I (I)

where the dashed line can be an additional C—C bond, $R^1$ is a branched or unbranched alkyl having from 1 to 4 carbons and $R^2$ is a saturated or unsaturated, branched or unbranched aliphatic hydrocarbon radical having from 1 to 37 carbons which may be unsubstituted or substituted by one or more methoxy groups, a cycloalkyl having from 4 to 12 carbons or a cycloalkyl alkyl having 5 to 30 carbons, preferably a group of the formula VI (VI)

where n is an integer from 1 to 6 and X and Y are either both H, or X is methoxy and Y is H, or X and Y together are an additional bond between the X- and Y-bearing carbons, can be prepared continuously in a single reactor with higher product yields and higher space-time yields by reacting an unsaturated alcohol of the formula II (II)

where $R^1$ and $R^2$ have the meanings given above, with an alkyl acetoacetate of the formula III (III)

where $R^3$ is a branched or unbranched alkyl having from 1 to 5 carbons, in the presence of organic aluminum compounds as catalyst, by A. reacting the unsaturated alcohol of the formula II with the acetoacetic ester of the formula III on the internals (16) of a fractionation tower (4) to give the acetoacetate of the unsaturated alcohol of the formula II and separating off the resultant alcohol of the formula IV $R^3$—OH (IV)

with the overhead stream (5) of the fractionation tower and

B. rearranging the resultant acetoacetate of the alcohol of the formula II into the unsaturated ketone of the formula I in the presence of the organic aluminum compound in the lower part of the fractionation tower and/or in the bottom (20) of the fractionation tower, the carbon dioxide forming in this case passing via the fractionation tower (4) into the overhead stream (5) and the resultant unsaturated ketone of the formula I being separated off from the tower via the bottom (20).

Using the process according to the invention, selectivities of up to 99% based on the alcohol and 97% based on the alkyl acetoacetate are achieved. This means that in the event of possible recycling of the unreacted alcohol and alkyl acetoacetate, overall yields of virtually 100% can be achieved. The conversion rate is 95% based on the alcohol and 98% based on the alkyl acetoacetate, so that only small amounts of starting material need to be recirculated. The space-time yield is greater than with previously known processes by a factor of 3. In addition, the unwanted further reaction of the unsaturated ketones of the formula I, i.e. the reaction products, by Meerwein Ponndorf Verley reduction to the corresponding alcohols, can be avoided by the process according to the invention.

The process according to the invention may be applied in principle to all known variants of the Carroll reaction, with there being no restriction regarding the boiling points of the reactants. However, the process is of particular importance for the synthesis of those ketones which are required for preparing aroma substances and isophytol, such as geranylacetone, farnesylacetone, dihydrogeranylacetone, dihydrofarnesylacetone and 2-methyl-2-hepten-6-one.

A great advantage of the process according to the invention is that the high achievable yields are achieved in a continuous process in one reactor with virtually quantitative conversion based on all starting components, even if no excess or only a slight excess of one of the reaction components is used. In addition, it is a great advantage that the process according to the invention can increase the space-time yields of the previously known processes by a factor of 3.

The process according to the invention is of particular importance for the reaction of alcohols of the formula (IIa), where X, Y and n have the meanings given above, such as 3,7-dimethyl-1,6-octadien-3-ol (linalool), 3,7-dimethyl-1-octen-3-ol, 3,7,11-trimethyl-1,6,10-dodecatrien-3-ol (nerolidol), 3,7,11-trimethyl-1-dodecen-3-ol and 3,7,11-trimethyl-1,6-dodecadien-3-ol (dihydronerolidol).

The reaction is successful in principle in any alkyl acetoacetates, but for economic and processing reasons, preference is given to the methyl ester, ethyl ester and isopropyl ester, since the alcohols to be eliminated from these are particular low-boiling and can thus be readily removed from the reaction mixture. The use of tert-butyl acetoacetate is accompanied by the advantage of a more rapid reaction and the avoidance of by-products. The amounts of the reactants used are advantageously selected so as to give a molar ratio of alcohol of the formula II to alkyl acetoacetate of the formula III from 0.8 to 1.2, preferably from 0.95 to 1.10.

Suitable organic aluminum compounds for the process according to the invention are essentially compounds of the formula V where $R^4$ is branched or unbranched alkyl or alkoxy having from 1 to 4 carbons, preferably methyl or ethyl, $R^5$ and $R^6$ are branched or unbranched alkyl or alkoxy having from 1 to 5 carbons, preferably methyl or 2-butyl, $R^7$ is a branched or unbranched alkyl having from 1 to 4 carbons and m and n can be integers from 0 to 3, where $n+m \leq 3$, and also aluminum triaryloxylates. Particular preference is given to liquid aluminum compounds, in particular aluminum compounds where $R^5$ is a methyl, $R^6$ is a butyl and $n+m=3$ and $n/m>0.3$.

The catalysts mentioned first are therefore lower aluminum trialkoxides, such as aluminum trimethoxide, aluminum triethoxide, aluminum triisopropoxide, aluminum tri-sec-butoxide, and compounds which are formed in the reaction of said aluminum trialkoxides with stoichiometric amounts of acetylacetonate, alkyl acetoacetate or alkyl malonate with elimination of alcohol and transesterification. Specific examples are aluminum triacetoacetate, aluminum triacetyl acetonate, aluminum monoacetoacetate diethoxide, aluminum monoacetoacetate diisopropoxide, aluminum diacetoacetate monoisopropoxide.

Preferably, use is made of the aluminum trialkoxides, in particular aluminum triisopropoxide and aluminum tri-sec-butoxide. Very particularly preferably, use is made of mixed aluminum triacetoacetates which are produced by reacting aluminum sec-butoxide or aluminum triisopropoxide with methyl acetoacetate with elimination of 2-butanol or isopropanol and transesterification of the methoxy groups with the released 2-butanol or isopropanol, where the degree of transesterification is to be greater than 30%.

For the purposes of the invention, aluminum triaryloxylates are the aluminum salts of aromatic hydroxyl compounds such as aluminum triphenolate, aluminum tricresolates, aluminum trixylenonlates, aluminum trinaphtholates, whose aryl radicals can also be substituted by lower alkyl or alkyloxy, i.e. alkyl or alkyloxy having from 1 to 4 carbons, hydroxyls or phenyl. Particularly advantageously, of these, use is made of the relatively readily accessible aluminum triphenolate.

It is advantageous to use liquid catalysts or solutions of solid catalysts and to feed these in liquid form into the fractionation tower, preferably into the bottom (20) of the tower. Thus use can be made of, for example, aluminum trialkoxides dissolved in alkyl acetoacetate or dissolved in a mixture of alkyl acetoacetate and an alcohol of the formula II.

The amount of the aluminum compound is generally such that its concentration does not fall below 0.05% by weight of Al in the reaction mixture and does not exceed 6% by weight of Al at the start of the reaction. Based on alkyl acetoacetate to be reacted, generally from 0.5 to 5 mol % of the aluminum compound is required. For the aluminum triisopropoxide preferably used and the above described mixed aluminum triacetoacetate prepared from aluminum sec-butoxide and methyl acetoacetate, amounts of, for example, from about 1 to 3 mol %, based on the alkyl acetoacetate to be reacted, are used.

Figure 1:
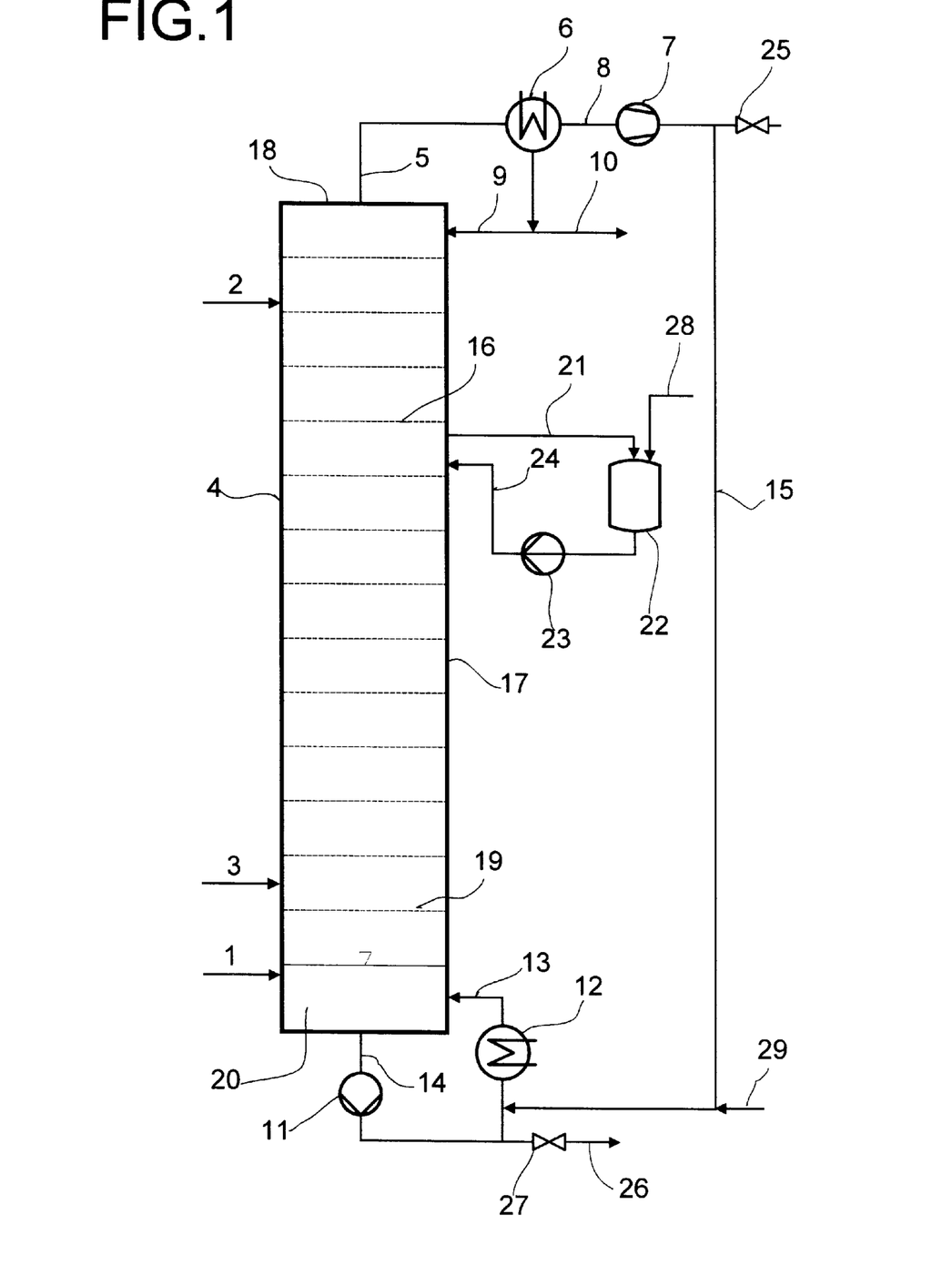
FIGS. 1 and 2 describe the two reactors employed in the continuous process.

An advantageous procedure for the process according to the invention is described below with reference to FIG. 1.

The process according to the invention is expediently carried out in such a manner that the alcohol of the formula II, the acetoacetic ester of the formula III with or without the aluminum compound of the formula V is applied via the feeds (2) and (3) and/or (1) to the internals of a fractionation tower as reaction tower (4). It is advantageous here, but not compulsory if the higher-boiling reactant is fed continuously into the fractionation tower (4) separately or together with the catalyst of the formula (V) above the lower-boiling reactant. The reaction of the unsaturated alcohol of the formula II with the acetoacetic ester of the formula III to form the acetoacetate of the alcohol of the formula II then takes place on the fractionation tower internals together with a superimposed distillation. As a result, the alcohol of the formula IV which is formed from the alkyl acetoacetate is continuously removed from the reaction mixture, which gives rise to an advantageous equilibrium position. The acetoacetate of the alcohol of the formula II formed as intermediate distils into the lower part (19) of the fractionation tower (4), where, at relatively high temperatures (from 120 to 220° C.), it is rearranged and cleaved in the presence of the aluminum compound of the formula V acting as catalyst. The carbon dioxide formed in the course of this passes via the fractionation tower (4) into its overhead stream (5).

The aluminum compound can be fed in at any point of the fractionation tower. However, particularly advantageously, it is introduced into the lower part of the column or even into the bottom, since it is only required here as catalyst for the rearrangement and elimination of acetoacetate from the alcohol of the formula II.

When use is made of methyl or ethyl acetoacetate as ester of the formula III, it is very advantageous if this ester is introduced into vaporous form into the tower (4), since then the formation of the acetoacetate of the alcohol of the formula II proceeds more rapidly.

Furthermore, it has proven to be highly advantageous if the heat is supplied to the reactor system consisting of tower bottom (20) and fractionation tower (4) with or without vessel (22) not only via the evaporator (12), but in addition via external heat exchangers (17) or via heat exchangers situated directly on the trays (16).

The resultant carbon dioxide and the alcohol of the formula IV leave the tower together with the low-boilers as overhead stream (5) and pass into the condenser (6) where the condensable constituents of this vapor stream are condensed out. Some of the condensate is reapplied to the tower as reflux (9) and the remainder (10) is taken off. A reflux ratio of from 1 to 10, preferably from 2 to 4, should be set. However, it is also possible to take-off the condensate completely (reflux ratio=0), if the higher-boiling reactant is applied at the upper end of the tower. The carbon dioxide leaves the condenser (6) via the exhaust gas line (8). The pressure at the tower top (18) is set so that the temperature in the bottom (20) is from 120 to 300° C., preferably from 160 to 230° C., in particular from 170 to 220° C. Depending on the material system and desired bottom temperature, this can be achieved using a vacuum pump (7) and/or a pressure control device (25).

The reaction product collects in the bottom (20) of the tower (4) and is taken off using a pump (11) together with the unreacted reactants via the bottom stream (14). The crude product is discharged via the product line (26) using a control valve (27) and fed to further workup. Some of the bottom stream (14) is evaporated in an evaporator (12) and fed back to the tower via the vapor line (13). It is possible, for removal of the resultant alcohol of the formula IV, to feed additionally an inert gas (29) into the bottom or the lower part of the column and/or, for this purpose, to recirculate into the column (4) via the line (15) the carbon dioxide which is formed and discharged together with the overhead stream.

The metering rates are selected so that the stoichiometric ratio of the alcohol of the formula II to the acetoacetic ester of the formula III is from 0.8 to 1.2, preferably from 0.95 to 1.10 and a catalyst content from 0.1 to 5 mol %, preferably from 1 to 3 mol %, based on the alkyl acetoacetate to be reacted is set. The residence time of the reaction mixture in the reactor system consisting of tower bottom (20) and fractionation tower (4), with or without the vessel (22), should be from 15 minutes to 6 hours, preferably from 1 to 4 hours. It can be set advantageously, if, as tower internals, use is made of trays (16) having a high liquid residence time, such as valve trays, preferably bubble-cap trays, or related types, such as tunnel-cap trays. However, it is likewise possible to use metal cloth packings or metal sheet packings having an arranged structure or else dumped packings as tower internals. In addition, it is likewise possible, for increasing the residence time, to pass a partial stream through one or more sidestream take-offs (21) from the fractionation tower (4) through the vessel or vessels (22) and, using a pump (23) for each, to recirculate the partial streams (24) leaving these vessels back into the tower (4). If necessary, additional catalyst and/or reactants can be added to the vessels (22) using a feed line (28). Heating the vessels (22) is expedient.

To carry out the reaction, advantageously, use is made of fractionation towers which have as internals from 10 to 100 of the trays (16) described in more detail above, preferably from 20 to 40 trays. In this case, advantageously, operations are carried out in such a manner that the higher-boiling reactant is introduced into the upper part of the tower and the lower-boiling reactant is introduced into the lower part of the tower. It has proved to be particularly advantageous if, in the tower, from 0 to 5 trays are present above the feed (2) for the higher-boiling reactant and, in the lower part (19) of the tower, from 0 to 5 trays are present below the feed (3) for the lower-boiling reactant. The residence time on the tower internals should be about 30 minutes. The equivalent applies to the theoretical plates in the case of other tower internals.

When the crude product stream (14) from the crude product line (26) is worked up, it is advantageous firstly to separate off the catalyst using an evaporator and then to isolate the product of value in subsequent distillation towers. Unreacted reactants can be recirculated to the fractionation tower (4). The use of a dividing-wall tower has proved to be highly advantageous in the work-up of the crude product stream.

Figure 2:
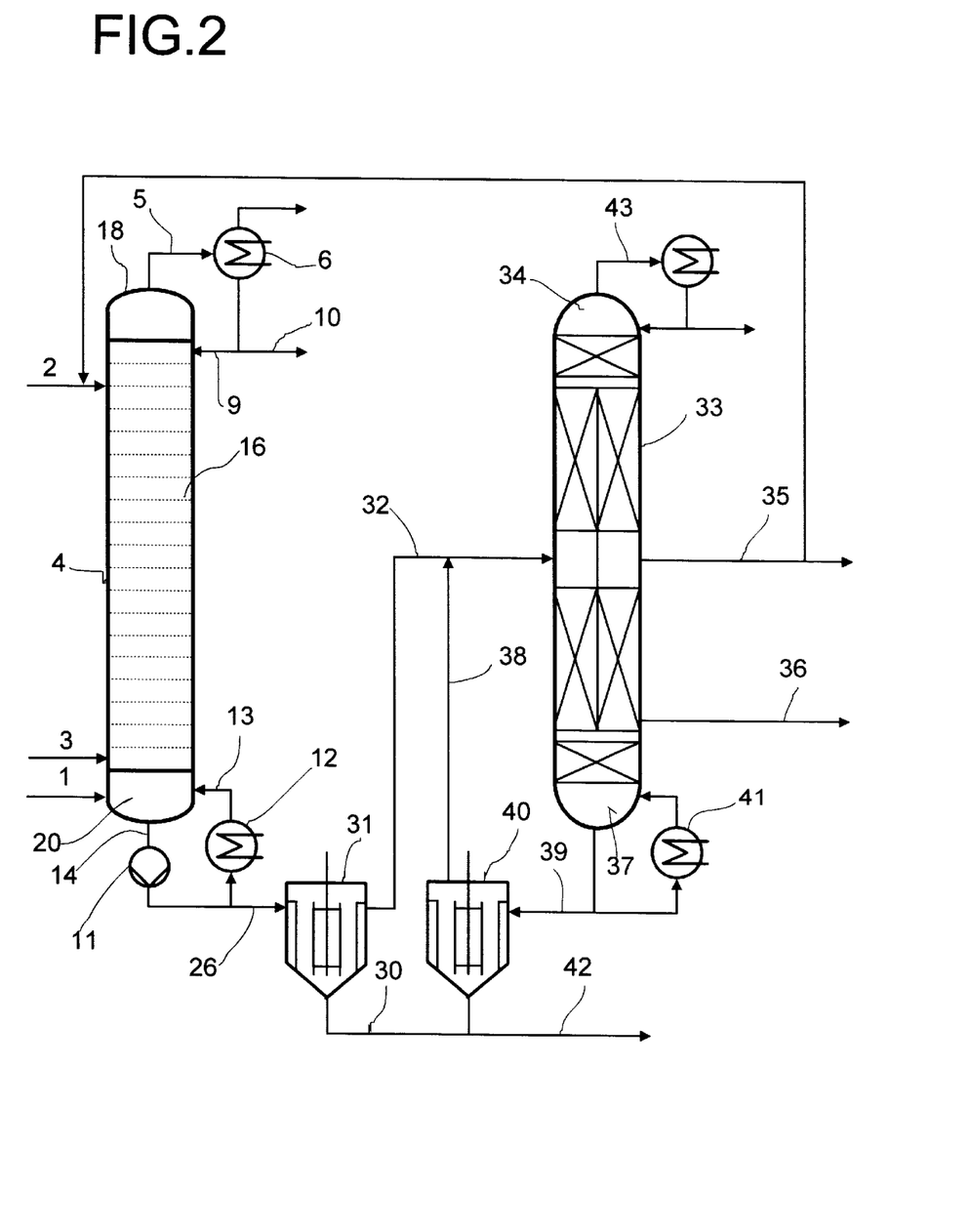

As example of the crude product stream workup, workup using a dividing-wall column is described in more detail below with reference to FIG. 2.

When the crude product stream (14) from the crude product line (26) is worked up, it is advantageous firstly to separate off a mixture (30) of the catalyst and high-boilers using an evaporator (31). This decreases the decomposition of product of value in the following workup stages. The catalyst (30) separated off can be fed in whole or in part to the reaction tower. The catalyst-free mixture (32) of product of value, unreacted reactants and low-boiling by-products is then fractionated in downstream distillation towers. For this separation task, usually two conventional distillation towers are required. However, preference is given to the use shown in FIG. 2 of a dividing-wall tower (33), using which, for example, the lower-boiling reactant can be separated off overhead (34), the higher-boiling reactant can be separated off via a side stream take-off (35), the unsaturated ketone of the formula I can be separated off via a further sidestream take-off (36) and the high-boilers can be separated off via its bottom (37). Since, using a dividing-wall tower, the desired separation is possible in a single apparatus instead of two distillation towers, capital costs are saved.

The invention therefore also relates to the process described in more detail above in which the crude product separated off via the bottom (20) of the fractionation column and ejected via the product line (26) for workup is fractionated in a downstream dividing-wall tower (33) either directly or after separating off the mixture (30) from the catalyst and high-boilers by means of an evaporater (31).

The unreacted higher-boiling reactant can be recirculated to the reaction tower (4) via the inlet (2) to increase the yields. It is likewise possible to recirculate the unreacted lower-boiling reactant to the reaction tower (4), with or without discharge of a partial stream. However, in practice, complete reaction regarding the ester of the formula III is preferably sought after, so that the overhead stream (43) comprising low-boiling minor components is usually completely discharged from the dividing-wall tower and disposed off. The bottom stream (39) comprising high-boilers and products of value is passed through a second evaporator (40) in which the high-boilers are separated off as bottom stream (42). The stream (38) comprising the product of value is recirculated to the dividing-wall column (33).

In some applications of the process of the invention, for example in the preparation of 2-methyl-2-hepten-6-one the ester of the formula III boils above the alcohol of the formula II. In this case, it is more advantageous to recirculate the overhead stream (43), possibly after ejecting a partial stream, to the reaction tower (4). The complete ejection described above is not expedient in this case. The ester of the formula III can be taken off together with the side stream (35) and, possibly after ejecting a partial stream, can be recirculated to the reaction tower (4).

To save capital expenditure, it is also possible to use, instead of the two evaporators (31) and (40), only a single evaporator. It is likewise possible to pass the crude product stream (26) directly into the dividing-wall tower (33) and to dispense with the evaporator (31). In this case, care must be taken to ensure that the residence time in the bottom (37) and evaporator (41) of the dividing-wall tower is kept short in order to avoid the decomposition of product of value. The residence time in the bottom of the dividing-wall tower should expediently be less than 1 hour. In this case, the bottom stream (39) is freed in the evaporator (40) from catalyst and high-boilers and the stream (38) comprising the product of value is recirculated to the dividing-wall tower (33). The catalyst separated off in the bottom stream (42) can wholly or partially be recirculated to the reaction tower (4).

Using the process improved according to the invention it is possible to prepare numerous higher ketones, in particular those ketones as are required for preparing isophytol and thus for preparing vitamin E, such as geranylacetone, farnesylacetone, 6,10-dimethyl-5-undecen-2-one, 6,10,14-trimethyl-5,10-pentadecadien-2-one and 2-methyl-2-hepten-6-one, with virtually quantitative conversion in very high yields and space-time yields and high purity. Using the process according to the invention it is also possible to react a mixture of two different unsaturated alcohols of the formula II with an alkyl acetoacetate of the formula III to form a mixture of the corresponding unsaturated ketones of the formula I and then to work up this mixture by distillation. This is advantageous, for example, if it is wanted to prepare changing amounts of different unsaturated ketones, but the amounts of ketone required are not so great that a separate production plant must be built for each ketone.

EXAMPLE 1

Preparation of 6,10-dimethyl-5-undecen-2-one (dihydrogeranyl-acetone)

A. Description of the Apparatus

The apparatus used was a fractionation tower (4) having 30 bubble-cap trays (approximately 20 theoretical plates) and an internal diameter of 30 mm. The trays were numbered from bottom to top, i.e. the lowest tray was tray 1 and the topmost tray was tray 30. The tower was fitted at regular distances with thermocouples, so that, except at the bottom (20) and at the top (18) of the tower, at each third to fourth theoretical plate, the temperature could be measured. In addition to the temperature profile, using appropriate sample take-off points, the concentration profile in the tower could be determined. The evaporator (12), which was heated to 250° C. using a thermostat, had a volume of approximately 350 ml, with the filling level during operation being about 225 ml. A cooler (6), which was operated by a cryostat, was mounted on the tower. In addition, the tower was equipped with a vacuum unit (7) and a cold trap. All incoming and outgoing streams were recorded and displayed using balances.

B. Experimental Procedure—Preparation of 6,10-dimethyl-5-undecen-2-one 135.0 g/h (0.81 mol/h) of 3,7-dimethyl-1-octene-3-ol (dihydrolinalool, 94% strength) were applied to tray 27 of the tower (4) and 94.0 g/h (0.81 mol/h) of methyl acetoacetate (AME) were applied to tray 3 of the tower. The catalyst used was a mixed aluminum triacetoacetate in the form of a methanolic solution prepared by reacting aluminum sec-butoxide with AME. The catalyst was characterized by elemental analysis and $^1$H-NMR, which gave an aluminum content of 5.0% by weight and a degree of transesterification (methanol against 2-butanol) of 50%. 7.6 g/h (1.5 mol % of aluminum based on AME used) of this catalyst were metered onto tray 27, together with the 3,7-dimethyl-1-octene-3-ol. A system pressure of 500 mbar and a reflux ratio of 3 was set.

The bottom temperature was 200° C. and the residence time in the reactor system was 2 hours. As bottom stream, 171.7 g/h of crude product comprising 87.4% by weight of 6,10-dimethyl-5-undecen-2-one, 3.8% by weight of 3,7-dimethyl-1-octen-3-ol, 0.4% by weight of AME and 8.4% by weight of high-boilers were obtained. At the top (18) of the tower, 23.3 g/h of distillate comprising 89.5% by weight of methanol were taken off. The carbon dioxide formed during the reaction was removed from the column overhead (18). The 6,10-dimethyl-5-undecen-2-one was obtained with a selectivity of 99.2%, based on 3,7-dimethyl-1-octen-3-ol and 95.4% based on AME. The degree of conversion was 95%, based on 3,7-dimethyl-1-octen-3-ol, and 99.2%, based on AME. From the crude product, in a distillation tower having 22 theoretical plates, 6,10-dimethyl-5-undecen-2-one was obtained in a purity of 99.99%.

EXAMPLE 2

Preparation of 6,10,14-trimethyl-5,10-pentadecadien-2-one dihydrofarnesylacetone)

A. Continuous Preparation According to the Invention

In the apparatus described in Example 1, 152.0 g/h (0.63 mol/h) of 3,7,11-trimethyl-1,6-dodecadien-3-ol (dihydronerolidol, 93% strength) were applied to tray 27 of the tower and 73.0 g/h (0.63 mol/h) of AME were applied to tray 3 of the tower. The catalyst used was a mixed aluminum triacetoacetate as an 80% strength methanolic solution prepared by reacting aluminum sec-butoxide with AME. The catalyst was characterized by elemental analysis and $^1$H-NMR, which gave an aluminum content of 5.4% by weight and a degree of transesterification (methanol against 2-butanol) of 50%. 4.9 g/h (1.5 mol % of aluminum, based on AME) of this catalyst were metered onto tray 27 together with the 3,7,11-trimethyl-1,6-dodecadien-3-ol. A system pressure of 500 mbar and a reflux ratio of 3 were set. The bottom temperature was 200° C. and the residence time in the reactor system was 2 hours. 180.4 g/h of crude product comprising 82.3% by weight of 6,10,14-trimethyl-5,10-pentadecadien-2-one, 5.3% by weight of 3,7,11-trimethyl-1,6-dodecadien-3-ol, 1.1% by weight of AME and 11.3% by weight of high-boilers were obtained as bottom stream. At the top of the tower, 14.6 g/h of distillate consisting of 88.1% by weight of methanol were taken off. The carbon dioxide formed during the reaction was taken off from the tower overhead. The 6,10,14-trimethyl-5,10-pentadecadien-2-one was obtained with a selectivity of 95.6% based on 3,7,11-trimethyl-1,6-dodecadien-3-ol and 91.7% based on AME. The degree of conversion was 93.5%, based on 3,7,11-trimethyl-1,6-dodecadien-3-ol and 97.4% by weight based on AME.

B. Batchwise Comparative Experiment

The experimental apparatus consisted of a heatable stirrer-equipped 2-liter stainless steel reaction flask, on which was mounted a distillation tower (length: 1 m, diameter: 25 mm). The tower was packed with stainless steel wire coils (5 mm). The reactants were either introduced into the reaction still or added using a pump. The components methanol and $CO_2$, released during the reaction were separated off via the tower and condensed. All incoming and outgoing streams were continuously recorded and registered during the entire experiment, so that a time-dependent mass balance was possible.

657.6 g (2.73 mol) of 3,7,11-trimethyl-1,6-dodecadien-3-ol (dihydronerolidol, 93% strength) were placed in a reaction flask having an attached column and heated to 100° C. 27.7 g (1.5 mol % based on AME) of the above described catalyst solution were then mixed with 35.4 g (0.15 mol) 3,7,11-trimethyl-1,6-dodecadien-3-ol and 7.5 g (0.06 mol) of AME, the mixture was added to the flask contents and the reaction mixture was heated to 175° C. 326.5 g (2.82 mol) of AME were then metered into the reaction still in the course of 3.5 h. During the AME addition, the reaction solution was heated further and the temperature controlled to 185° C. At the start of the AME addition, $CO_2$ development began, and the methanol formed was taken off as distillate. The reflux ratio was 0.1. After approximately 3.5 h, the AME metering was completed. At the completion of the AME metering, the post-reaction began. The temperature was also kept constant at 185° C. during the post-reaction. The post-reaction was terminated after 2 h. The 6,10,14-trimethyl-5,10-pentadecadien-2-one was thus obtained with a selectivity of 93.9% based on 3,7,11-trimethyl-1,6-dodecadien-3-ol and 91.8% based on AME.

EXAMPLE 3

Preferred Procedure for Preparing Dihydrofarnesylacetone

In the apparatus described in Example 1, 155.0 g/h (0.64 mol/h) of 3,7,11-trimethyl-1,6-dodecadien-3-ol (dihydronerolidol, 92% strength) were pumped onto tray 27 of the tower (4). In contrast to example 2, 74.0 g/h (0.64 mol/h) of AME were metered in the vapor state into the vapor space above the bottom (20) of the tower (4). The catalyst used was a mixed aluminum triacetoacetate, which had been prepared by batch reaction of 500 g (2.03 mol) of aluminum tri-sec-butoxide with 707 g (6.09 mol) of AME. The catalyst which—owing to its preparation as solution—was used with approximately 18% by weight of 2-butanol and 6% by weight of methanol, was characterized by elemental analysis and $^1$H-NMR. This gave an aluminum content of 4.4% by weight and a degree of transesterification (methanol against 2-butanol) of approximately 50%. 6 g/h of the catalyst solution (1.5 mol % of aluminum based on AME) were, in contrast to Example 1, pumped directly into the bottom (20). A system pressure of 500 mbar and a reflux ratio of 3 were set. The temperature in the bottom (20) was 200° C. and the residence time in the reactor system was 2 hours. The bottom stream (14) produced was 182.7 g/h of crude product comprising 82.7% by weight of 6,10,14-trimethyl-5,10-pentadecadien-2-one, 4.9% by weight of 3,7,11-trimethyl-1,6-dodecadien-3-ol, 1.0% by weight of AME and 11.4% by weight of high-boilers. 16.7 g/h of distillate consisting of 80.6% by weight of methanol and 8.6% by weight of 2-butanol were taken off at the top (18) of the tower as overhead stream (5). The carbon dioxide formed during the reaction was also taken off from the tower (4) overhead (18). The 6,10,14-trimethyl-5,10-pentadecadien-2-one was obtained with a selectivity of 96.0%, based on 3,7,11-trimethyl-1,6-dodecadien-3-ol and 91.8% based on AME. The degree of conversion was 93.7% based on 3,7,11-trimethyl-1,6-dodecadien-3-ol, and 97.7% based on AME. The crude product was worked up in a subsequent dividing-wall tower (33) having 30 theoretical plates, in which case the 6,10,14-trimethyl-5,10-pentadecadien-2-one was taken off via the sidestream take-off (36) at a purity of 99.99% and the unreacted 3,7,11-trimethyl-1,6-dodecadien-3-ol was taken off at a purity of 90% via the sidestream take-off (36).

EXAMPLE 4

Continuous Joint Production of Dihydrogeranylacetone and Dihydrofarnesylacetone

In the apparatus described under Example 1, 84.0 g/h (0.35 mol/h) of 3,7,11-trimethyl-1,6-dodecadien-3-ol (dihydronerolidol, 92% strength) and 58.5 g/h (0.34 mol/h) of 3,7-dimethyl-1-octen-3-ol (dihydrolinalool, 90.5% strength) were pumped onto tray 27 of the tower (4). 80.0 g/h (0.69 mol/h) of AME were metered onto tray 3 of the tower (4). The catalyst used was a mixed aluminum triacetoacetate, which had been prepared by batchwise reaction of 500 g (2.03 mol) of aluminum tri-sec-butoxide with 707 g (6.09 mol) of AME, without removing the 2-butanol released. The catalyst which—owing to its preparation as solution—was used with approximately 18% by weight of 2-butanol and 6% by weight of methanol, was characterized by elemental analysis and $^1$H-NMR. This gave an aluminum content of 4.4% by weight and a degree of transesterification (methanol against 2-butanol) of approximately 50%. 6.5 g/h of the catalyst solution (1.5 mol % of aluminum, based on AME) were pumped onto tray 27 of the tower (4). A system pressure of 500 mbar and a reflux ratio of 3 were set. The temperature in the bottom (20) was 200° C. and the residence time in the reactor system was 2 hours. As bottom stream (14), 172.0 g/h of crude product comprising 46.9% by weight of 6,10,14-trimethyl-5,10-pentadecadien-2-one, 36.1% by weight of 6,10-dimethyl-5-undecen-2-one, 2.7 by weight of 3,7,11-trimethyl-1,6-dodecadien-3-ol, 1.6% by weight of 3,7-dimethyl-1-octen-3-ol, 0.9% by weight of AME and 13.4% by weight of high-boilers were obtained. At the top (18) of the tower (4) 20.2 g/h of distillate consisting of 80.9% by weight of methanol and 11.3% by weight of 2-butanol were taken off as overhead stream (5). The carbon dioxide formed during the reaction was also taken off from the tower overhead (18). The 6,10,14-trimethyl-5,10-pentadecadien-2-one was obtained at a selectivity of 94.0%, based on 3,7,11-trimethyl-1,6-dodecadien-3-ol, and the 6,10-dimethyl-5-undecen-2-one was obtained at a selectivity of 98.4%, based on 3,7-dimethyl-1-octen-3-ol. The selectivity of the products of value, based on AME, was 91.9%. The degree of conversion was 94.1% based on 3,7,11-trimethyl-1,6-dodecadien-3-ol, 94.7%, based on 3,7-dimethyl-1-octen-3-ol and 98.2% based on AME.

EXAMPLE 5

Preparation of Dihydrofarnesylacetone in a Reaction Tower Having a Structured Packing A. Description of the Apparatus The reaction apparatus used was a distillation tower (4) having an internal diameter of 30 mm. The lower part of the tower was packed up to a height of 1 meter with a structured sheet metal packing (Sulzer Mellapak 250.Y). Above this sheet metal packing was 0.5 meters of a structured metal cloth packing (Sulzer DX). The tower (4) was fitted at regular distances with thermocouples, so that in addition to at the bottom (20) and at the top (18) of the tower, the temperature could be measured at a plurality of points in the tower. In addition to the temperature profile, using appropriate sample withdrawal points, the concentration profile in the tower (4) was determined. The evaporator, which was heated to 250° C. using a thermostat, had a volume of approximately 350 ml, with the filling level remaining above 225 ml during operation. A cooler (6) was mounted on the tower (4), which cooler was operated with a cryostat. In addition, the tower (4) was fitted with a vacuum unit (7) and a cold trap. All incoming and outgoing streams were recorded and displayed using balances.

Experimental Procedure

In the above described apparatus, 155.0 g/h (0.64 mol/h) of 3,7,11-trimethyl-1,6-dodecadien-3-ol (dihydronerolidol, 92% strength) were pumped onto the upper packing segment (DX packing). 74.0 g/h (0.64 mol/h) of AME were metered in the vapor form into the vapor space above the bottom (20). The catalyst used was the mixed aluminum triacetoacetate described in example 4. 6 g/h of this catalyst solution (1.5 mol % of aluminum, based on AME) were pumped into the tower 10 cm above the bottom (20). A system pressure of 500 mbar and reflux ratio of 3 were set. The bottom temperature was 200° C. and the residence time in the reactor system was 2 hours. As bottom stream (14) 184.9 g/h of crude product comprising 80.8% by weight of 6,10,14-trimethyl-5,10-pentadecadien-2-one, 6.1% by weight of 3,7,11-trimethyl-1,6-dodecadien-3-ol, 0.9% by weight of AME and 12.2% by weight of high-boilers were obtained. At the top (18) of the tower, 16.0 g/h of distillate consisting of 83.0% by weight of methanol and 4.2% by weight of 2-butanol were taken off. The carbon dioxide formed during the reaction was also taken off overhead (18). The 6,10,14-trimethyl-5,10-pentadecadien-2-one was obtained at a selectivity of 96.5% based on 3,7,11-trimethyl-1,6-dodecadien-3-ol and 90.8% based on AME.

The conversion rate was 92.1% based on 3,7,11-trimethyl-1,6-dodecadien-3-ol, and 97.6% by weight based on AME.

EXAMPLE 6

Preparation of 2-methyl-2-hepten-6-one
Continuous Preparation According to the Invention
A. Description of the Experimental Apparatus The apparatus used was a reaction tower operated under pressure. This reaction tower consisted of a heatable stirrer-equipped 2-liter stainless reaction flask having an attached distillation tower (length: 1.2 m, diameter: 54 mm). Tower internals used were structured cloth packings of the type Montz A3-750 and about 14 theoretical plates were implemented by this. The AME was added continuously at room temperature to the upper part of the reaction tower, 2-methyl-3-buten-2-ol was flashed into the vapor space of the reaction pot and the catalyst was metered in the liquid state into the reaction pot. The methanol and $CO_2$ liberated during the reaction and the volatile byproducts isoprene and acetone were removed via the tower. The low-boilers of the vapor stream produced at the tower top were condensed in a partial condenser, a part of the condensate running via a reflux divider into a receiver, while the other part was added to the column as reflux. The remaining exhaust gas stream which principally consisted of $CO_2$ was passed through a cold trap and then, for measurement of volume, through a gas meter. The reaction product was taken off continuously from the tower bottom (2-liter reaction pot) by means of a level controller. The catalyst and the high-boilers were separated off from the bottom product by single-stage distillation and the distillate was analyzed by gas chromatography. The distillate of the reaction tower was likewise analyzed by gas chromatography. The apparatus was equipped with a pressure controller and designed for a system pressure of 10 bar. All influent and effluent streams were continuously determined and recorded during the entire experiment, so that a time-dependent mass balance was possible.

B. Experimental Procedure 81.9 g/h (0.70 mol/h) of AME were metered continuously to stage 3 of the tower (the stages are numbered from top to bottom, the condenser corresponding to stage 0). 67.0 g/h of 2-methyl-3-buten-2-ol (MBE; 92% pure; 0.72 mol/h calculated at 100%) were flashed into the vapor space of the reaction pot. The catalyst used was a mixed aluminum triacetoacetate prepared by reacting aluminum sec-butoxide with methyl acetoacetate. The catalyst was characterized by elemental analysis and $^1$H-NMR, which gave an aluminum content of 4.6% by weight and a degree of transesterification (methanol against 2-butanol) of 50%. 8.2 g/h (2.0 mol % of aluminum, based on AME) of this catalyst were metered into the reaction pot. A system pressure of 1.5 bar and a reflux ratio of 5 kg/kg was set. The bottom temperature was 171° C. and the residence time in the reactor system was 3.7 hours. The bottom stream produced was 99.6 g/h of crude product containing 82.4% by weight of 2-methyl-2-hepten-2-one, 3.8% by weight of 2-methyl-3-buten-2-ol, 1.2% by weight of methyl acetoacetate, 0.3% by weight of methanol and 12.0% by weight of high boilers. The content of the unwanted byproduct 2-methyl-2-hepten-6-ol was less than 0.2% by weight. 23.7 g/h of distillate consisting of 85.5% by weight of methanol were taken off from the top of the tower. The carbon dioxide formed during the reaction was passed off overhead. 2-Methyl-2-hepten-6-one was obtained at a selectivity of 97.7%, based on 2-methyl-3-buten-2-ol, and 94.5%, based on methyl acetoacetate. The yield was 90.8%, based on 2-methyl-3-buten-2-ol, and 93.1% by weight, based on AME.

From the crude product, after separating off the high-boilers by means of a thin-film evaporator and rectification in a rectification tower having 30 theoretical plates, 2-methyl-2-hepten-6-one was obtained in a purity of 99.8%.

EXAMPLE 7

Preparation of 2-methyl-2-hepten-6-one
Batchwise Comparative Experiment
A. Description of the Experimental Apparatus The experimental apparatus consisted of a heatable, stirrer-equipped 2-liter stainless steel reaction flask on which was attached a distillation tower (length: 1 m; diameter: 25 mm). The tower was packed with stainless steel wire coils (diameter: 5 mm). The reactants could either be charged into the reaction pot or metered into the reaction pot using a pump from a reservoir which stands on a balance. The methanol and $CO_2$ liberated during the reaction, and the volatile byproducts isoprene and acetone, were removed via the distillation tower and the low-boilers were condensed in a partial condenser. The condensate ran via a reflux divider into a receiver. The remaining exhaust gas stream, which principally consisted of $CO_2$, was passed through a cold trap and then, for measurement of volume, through a gas meter. The apparatus was equipped with a pressure control apparatus and was designed for a system pressure of 10 bar. All influent and effluent streams were continuously determined and recorded during the entire experiment, so that a time-dependent mass balance was possible.

B. Experimental Procedure

680.0 g of 2-methyl-3-buten-2-ol (MBE; 93% pure; 7.34 mol calculated at 100%) and 96.7 g of catalyst (1.75 mol % of aluminum, based on AME) were charged into the 2-liter stirred autoclave having an attached tower. The catalyst used was mixed aluminum triacetoacetate prepared in a similar manner to Example 6 by reacting aluminum sec-butoxide with AME. Nitrogen was then injected in using a gas cylinder and a reactor pressure of 1.7 bar (absolute) was set. The mixture of MBE and catalyst was then heated with an infinite reflux ratio using the thermostat to 130° C. From a temperature of 130° C., 811.3 g (6.99 mol) of AME were added to the stirred autoclave within 180 minutes (min) in a linear manner. The reaction was initiated with the start of metering, so that the $CO_2$ development began. As a result, within 30 min, a reaction pressure of 4 bar (absolute) had built up. The pressure was then maintained via the pressure control apparatus.

In the start-up phase, MBE predominantly distilled into the tower, which was recycled to the stirred autoclave at total reflux. The MBE, at the start of metering, was displaced by the methanol liberated during the reaction. As soon as an overhead temperature of 104° C. (boiling point of methanol at 4 bar) had been reached, the reflux ratio (PR) was set to 14. The resultant methanol was separated off as distillate via the attached tower and the $CO_2$ was removed in such a manner using the pressure control apparatus that the reactor pressure was maintained at 4 bar. The temperature (T) of the reaction mixture increased during the reaction to 185° C. and was then controlled to 185° C. After 180 min, the AME metering was shut off. The post-reaction began with termination of the AME metering. The apparatus was slowly reduced in pressure from 4 bar to atmospheric pressure, during which the temperature (T) decreased from 185° C. to 170° C. The T was then controlled to 170° C. The post-reaction was terminated after 90 min. The catalyst and the high-boilers were separated off by single-stage distillation and the distillate was analyzed by gas chromatography.

2-Methyl-2-hepten-6-one was obtained at a selectivity of 93.4%, based on 2-methyl-3-buten-2-ol, and 89.0%, based on AME. The yield was 85.6%, based on 2-methyl-3-buten-2-ol, and 89.0% by weight, based on AME.

We claim:

1. A process for the continuous preparation of unsaturated ketones of formula I (I)

where the dashed line can be an additional C—C bond, $R^1$ is a branched or unbranched alkyl having from 1 to 4 carbons and $R^2$ is a saturated or unsaturated, branched or unbranched, unsubstituted or methoxy-substituted aliphatic hydrocarbon radical having 1 to 37 carbons, a cycloalkyl having from 4 to 12 carbons or a cycloalkylalkyl having 5 to 30 carbons, by reacting an unsaturated alcohol of the formula II (II)

where $R^1$ and $R^2$ have the meanings given above, with an alkyl acetoacetate of the formula III (III)

where $R^3$ is a branched or unbranched alkyl having from 1 to 5 carbons, in the presence of organic aluminum compound as catalyst which comprises

A. reacting the unsaturated alcohol of the formula II with the alkyl acetoacetate of the formula III on the internals of a fractionation tower to give the acetoacetate of the unsaturated alcohol and separating off the resultant alcohol of the formula IV $R^3$—OH (IV)

with the overhead stream of the fractionation tower and

B. rearranging the resultant acetoacetate of the alcohol of the formula II into the unsaturated ketone of the formula (I) in the presence of the organic aluminum compound in the lower part of the fractionation tower and/or in the bottom of the fractionation tower, the carbon dioxide forming in this case passing via the fractionation tower into the overhead stream and the resultant unsaturated ketone of the formula (I) being separated off from the fractionation tower via the bottom.

2. A process as claimed in claim 1, wherein the stage B, of the reaction is carried out in the presence of from 0.1 to 5 mol %, based on the alkyl acetoacetate to be reacted, of an organic aluminum compound of the formula V (V)

where $R^4$ is branched or unbranched alkyl or alkoxy having from 1 to 4 carbons, $R^5$ and $R^6$ are branched or unbranched alkyl or alkoxy having from 1 to 5 carbons, $R^7$ is a branched or unbranched alkyl having from 1 to 4 carbons and m and n can be integers from 0 to 3, where $n+m \leq 3$, or is carried out in the presence of aluminum triaryloxylates as catalyst.

3. A process as claimed in claim 1, wherein, as unsaturated alcohol of the formula II, use is made of one in which $R^1$ is $CH_3$ and $R^2$ is a group of the formula VI (VI)

where n is an integer from 1 to 6 and X and Y are either both H, or X is methoxy and Y is H, or X and Y together are an additional bond between the X- and Y-bearing carbons.

4. A process as claimed in claim 1, wherein the starting amounts are chosen to give a molar ratio of alcohol of the formula II to acetoacetic ester of the formula III from 0.8 to 1.2.

5. A process as claimed in claim 1, wherein the higher-boiling of the unsaturated alcohol and alkyl acetoacetate reactants is fed into the fractionation tower above the lower-boiling of said reactants.

6. A process as claimed in claim 1, wherein the catalyst is fed in liquid form into the bottom of the fractionation tower.

7. A process as claimed in claim 1, wherein the pressure at the tower top is set such that the temperature in the bottom is from 120 to 300° C.

8. A process as claimed in claim 1, wherein the residence time in the reactor system consisting of tower bottom and fractionation tower with or without a vessel connected to the fractionation tower by inlet and outlet lines, is from 15 minutes to 6 hours.

9. A process as claimed in claim 1, wherein, as internals for the fractionation tower, use is made of tower trays.

10. A process as claimed in claim 1, wherein heat is supplied to the reactor system consisting of tower bottom and fractionation tower with or without a vessel connected to the fractionation tower by inlet and outlet lines, not only via an evaporator, but, in addition, via external heat exchangers or via heat exchangers situated directly on the trays.

11. A process as claimed in claim 1, wherein a mixture of two different unsaturated alcohols of the formula II is reacted with an alkyl acetoacetate of the formula III to give a mixture of the corresponding unsaturated ketones of formula I and this mixture is then worked up by distillation.

12. A process as claimed in claim 1, wherein the crude product separated off via the bottom of the fractionation tower and ejected via the product line for workup is fractionated in a downstream dividing-wall tower either directly or after separating off the mixture from the catalyst and high-boilers by means of an evaporator.

13. A process as claimed in claim 2, wherein $R^4$ is independently methyl or ethyl, and $R^5$ and $R^6$ are independently methyl or 2-butyl.

* * * * *